United States Patent
Chico Roca

(10) Patent No.: US 8,403,930 B2
(45) Date of Patent: Mar. 26, 2013

(54) FIXATION DEVICE FOR THE FIXATION OF BONE FRAGMENTS

(75) Inventor: Lluis Chico Roca, Badalona (ES)

(73) Assignee: Neos Surgery, S.L., Cerdanyola del Valles (ES)

( * ) Notice: Subject to any disclaimer, the term of this patent is extended or adjusted under 35 U.S.C. 154(b) by 139 days.

(21) Appl. No.: 12/671,165

(22) PCT Filed: Aug. 5, 2008

(86) PCT No.: PCT/EP2008/060279
§ 371 (c)(1),
(2), (4) Date: May 12, 2010

(87) PCT Pub. No.: WO2009/021876
PCT Pub. Date: Feb. 19, 2009

(65) Prior Publication Data
US 2010/0298828 A1    Nov. 25, 2010

(30) Foreign Application Priority Data
Aug. 10, 2007   (ES) .................................. 200702258

(51) Int. Cl.
*A61B 17/56* (2006.01)
*A61B 17/58* (2006.01)
*A61B 17/82* (2006.01)
*A61F 2/30* (2006.01)

(52) U.S. Cl. ............... 606/74; 606/324; 606/70; 606/71

(58) Field of Classification Search ............ 606/74, 606/70, 71, 282, 285, 324, 328; 24/16 PB
See application file for complete search history.

(56) References Cited

U.S. PATENT DOCUMENTS

| | | | |
|---|---|---|---|
| 3,926,193 A * | 12/1975 | Hasson | .................. 606/218 |
| 4,119,091 A | 10/1978 | Partridge | |
| 4,456,006 A | 6/1984 | Wevers et al. | |
| 5,449,359 A | 9/1995 | Groiso | |

(Continued)

FOREIGN PATENT DOCUMENTS

| DE | 103 47 173 B3 | 6/2005 |
|---|---|---|
| EP | 0 201 905 A2 | 11/1986 |

(Continued)

OTHER PUBLICATIONS

Spanish Search Report for ES 200702258, dated Mar. 22, 2010.

*Primary Examiner* — Andrew Yang
*Assistant Examiner* — Olivia C Chang
(74) *Attorney, Agent, or Firm* — Tim L. Kitchen; Peter B. Scull; Hamilton, DeSanctis & Cha, LLP

(57) ABSTRACT

A fixation device for the fixation of bone fragments, applicable to the mutual fastening of bone fragments temporarily separated during a surgical operation or as a result of a trauma. The device is also suitable for the fixation of a bone flap in the replacement thereof in a corresponding aperture made in the cranium or cranial bone mass. The device is made of biocompatible material and has a flexible strip and fastening mechanism, the strip having a length allowing the formation of a fastening loop tightly fastening the bone fragments to be joined together. The fastening mechanism is provided with at least one opening provided with an interlocking mechanism allowing the passage of a free end of the strip and preventing its extraction in the direction opposite to the insertion.

15 Claims, 6 Drawing Sheets

U.S. PATENT DOCUMENTS

| | | |
|---|---|---|
| 5,743,913 A | 4/1998 | Wellisz |
| 5,788,698 A | 8/1998 | Savornin |
| 5,810,854 A | 9/1998 | Beach |
| 6,022,351 A | 2/2000 | Bremer et al. |
| 6,050,998 A | 4/2000 | Fletcher |
| 6,589,246 B1 | 7/2003 | Hack et al. |
| 6,921,401 B2 | 7/2005 | Lerch et al. |
| 6,969,391 B1 | 11/2005 | Gazzani |
| 7,238,188 B2 | 7/2007 | Nesper et al. |
| 2004/0034375 A1 | 2/2004 | Ruiz et al. |
| 2004/0102779 A1* | 5/2004 | Nesper et al. ............ 606/72 |
| 2004/0116961 A1 | 6/2004 | Nesper et al. |
| 2005/0240189 A1 | 10/2005 | Rousseau et al. |
| 2006/0259040 A1* | 11/2006 | Wellisz et al. ............ 606/72 |
| 2007/0270856 A1* | 11/2007 | Morales et al. ............ 606/72 |

FOREIGN PATENT DOCUMENTS

| | | |
|---|---|---|
| EP | 1 171 050 B1 | 10/2004 |
| EP | 1 477 122 A2 | 11/2004 |
| FR | 2 357 229 A | 2/1978 |
| WO | 00/49949 A1 | 8/2000 |

\* cited by examiner

FIXATION DEVICE FOR THE FIXATION OF BONE FRAGMENTS

CROSS REFERENCE TO RELATED APPLICATIONS

This application is a National Stage of International Application No. PCT/EP2008/060279 filed Aug. 5, 2008, claiming priority based on Spanish Patent Application No. P 200702258, filed Aug. 10, 2007, the contents of all of which are incorporated herein by reference in their entirety.

TECHNICAL FIELD OF THE INVENTION

The invention relates to a fixation device for the fixation of bone fragments, applicable to the mutual fastening of bone fragments temporarily separated during a surgical operation or as a result of trauma. The device according to the invention is also suitable for the fixation of a bone flap in the replacement thereof in a corresponding aperture made in the cranium or cranial bone mass.

BACKGROUND OF THE INVENTION

When under certain circumstances bone tissue is fractured or broken, it must be welded together again in order to recover its initial state. To that end there are many different devices which are used in the event of breaking due to trauma or accident, or in the event that bone tissue must be previously broken or fractured in the operating room in order to perform surgery.

The devices used to join bone fragments generally consist of clamps, the parallel ends of which are inserted into each of the bone fragments to be joined together. An example of this type of device is the one described in patent EP 1171050 B1, in which the two fragments of the sternum that must be joined together after a surgical operation on the chest (cardiovascular, pulmonary . . . ) are fixed by the action of a C-shaped clamp with a center piece from which ends opposite to one another originate, said clamp provided with a loop in the area of the center piece which is deformed when cooled to be able to apply the ends to the bone fragments of the sternum and which, once applied on the bone mass, returns to its original shape when it reaches body temperature, comprising the mentioned ends and therefore the joining of the fragments.

Other clamp-shaped devices are described, each having its own particularities, in patent documents U.S. Pat. Nos. 5,449, 359, 5,788,698, 4,456,006 and U.S. Pat. No. 484,328.

Alternatively, surgical connectors can also be used to join bone fragments such as the connector described in U.S. Pat. No. 5,743,913 A1, in which a slightly curved plate provided with multiple openings and nodes homogenously distributed therethrough comprises at least three also slightly curved extensions or ribs joined to at least three of these nodes and suitable for receiving fastening means, such as screws.

All these devices involve the drawback that they are difficult to apply, requiring the use of applicator devices and/or additional instruments that are also very complex, or requiring additional elements for securing them in the bone fragments that must be joined together.

In the same manner, devices are widely used in the field of neurosurgical operations for the fixation of flaps or bone fragments which are generally provided with means for the fastening of the flaps, and suitable for being supported on or containing the cranial bone mass in a space reserved for such purpose, or by incision by means of a sharp element in said cranial mass. These devices are placed between the flap and the cranial bone, and except in the event that they are made of a biodegradable or absorbable material, they are permanently placed in the cranium.

One of the existing and widely used types of flap fixation devices generically consists of a device with two considerably circular elements facing one another in the form of semi-spherical caps joined by means of a shaft or shank through which the semi-spherical elements can be moved closer to one another in order to adjust the device to the cranium and flap bone mass thickness. Once the mentioned device is adjusted, both the flap and the cranial bone mass are supported between the semi-spherical elements, forming the bearing and supporting means of the flap and of the cranium. In this type of device, the neurosurgeon cuts the excess remaining shank once it is well placed between bone masses.

Patent document EP 1477122 A2 describes a device such as those described in the preceding paragraph consisting of an implant for adjacent cranial bone fragment fixation, comprising two fastening elements, an end element and an inner element, which by means of a joining element, which is wire, that is adjustable and can be led through the external fastening element, causes the sliding of the inner fastening element, which comes close to the external fastening element, said wire being led through multiple openings made in the fastening elements. The device described in EP1477122 A2 comprises additional joining means between the internal and external fastening elements, such as shafts perpendicular to the mentioned internal and external fastening elements, which can consist of ratchet teeth systems, clips or fragments with a trapezium- or triangular-shaped longitudinal section with side-projecting tips.

Patent document WO00/49949 likewise describes a fixation system comprising a fastening element of biocompatible material consisting of a disk-shaped head and a shank, in which said shank has a surface having ratchet teeth thereon, said fastening element consisting of a second, also disk-shaped, closure element, provided with an opening through which the shank can be inserted for the purpose of bringing the two disk-shaped elements together until the upper and lower edges of the bone fragments to be joined together.

These types of devices such as those described in patent document WO00/49949 are difficult to manufacture and store because of their size and because of the fact that they consist of an element from the central part of which there extends a shaft that is integral and perpendicular to the plane defined by the same, and they are subjected to a more demanding load state since the load is concentrated in the joint between the shaft and the disk-shaped head, whereby existing a higher probability of failure, especially when it is made with non-metallic materials.

Furthermore, many of these devices comprising two plates or elements joined by a rigid shaft involve the drawback that their entire surface does not adapt to different thicknesses and irregularities of the cranium and/or flap, resulting from the actual anatomy of this party of the body.

Most of these devices, specially designed to join bone flaps to the cranial bone mass, must be applied with the use of complex instruments, such as applicators suitable for engaging the shaft or shank joining the disk-shaped elements; and provided with means of pushing one of said disks, which is moved over the mentioned shaft in order to be close to its homologue.

The object of this invention provides novel solutions to the problems of manufacture, storage, resistance, adaptation to bone thicknesses and placement of bone fragment particularly bone flap, fixation devices. It is furthermore easy to apply due to simple elements provided in the actual fixation device and allows the possibility of being adjusted without the need for additional instruments.

DISCLOSURE OF THE INVENTION

The fixation device for the fixation of bone fragments object of the present invention is essentially characterized in that, being made of biocompatible material, it comprises a flexible strip and fastening means, the strip having a length allowing the formation of a fastening loop tightly fastening the bone fragments to be joined together, the fastening means being provided with at least one opening provided with interlocking means allowing the passage of a free end of the strip and preventing its extraction in the direction opposite to its insertion.

According to another variant of the invention, particularly intended for the fixation of a bone flap in the replacement thereof in a corresponding aperture made in the cranium or cranial bone mass, the device comprises two essentially planar plates connected by means of the flexible strip, one of which plates is a closure plate, intended for being applied against a face of the bone fragments, provided with the fastening means; and the other plate is a support plate, intended for being applied against another face of the mentioned bone fragments.

According to a preferred embodiment, the support plate is arranged integral and forming a single piece with the strip, or longitudinally movable, between the two ends of the mentioned strip, forming an assembly which is susceptible of adopting an essentially planar position in an inoperative position.

According to another feature of this variant of the invention, the closure plate is a detachable plate, the fastening means being provided with two openings for the passage of respective opposite ends of the strip.

The embodiment of the device according to claim 3 incorporates auxiliary gripping means making it easier to handle the device and regulate the tightness of the closure plate against the outer face of the bone fragments.

According to another variant of the invention, also intended for the fixation of a bone flap in an aperture made in the cranium, the closure plate is integral with one of the ends of the strip, forming a single piece with the strip, the fastening means being provided with an opening for the passage of the opposite end of the strip.

Claims 5 and 6 present different embodiments of interest for the support plate, while claim 7 presents a preferred embodiment for the closure plate, intended for improving the fastening and adaptability to the contour of the cranial bone mass.

With regard to the configuration of the strip, according to another feature of the invention, such strip is provided with a rough surface on at least one of its faces, a series of projections being formed which are suitable for collaborating with the interlocking means of the opening or openings, as the case may be, of the irreversible fastening means.

BRIEF DESCRIPTION OF THE DRAWINGS

The attached drawings show by way of a non-limiting illustration several embodiments for a fixation device for the fixation of bone fragments according to the invention. In said drawings:

FIGS. 3 to 7 are depictions of different variants, or views of one and the same variant, of devices suitable for the fixation of a bone flap in an aperture made in the cranium or cranial bone mass, of which:

FIG. 3 is a perspective view of a third variant of the device in an inoperative position, in which it has an essentially planar shape;

FIG. 4 is a perspective view of a fourth variant of the device also in an inoperative position, in which it has an essentially planar shape;

FIG. 5 is a view of the device according to FIG. 4 during a surgical intervention;

FIG. 7 is a view of the device according to FIG. 3 provided with auxiliary gripping means.

DETAILED DESCRIPTION OF THE DRAWINGS

Figure 1:
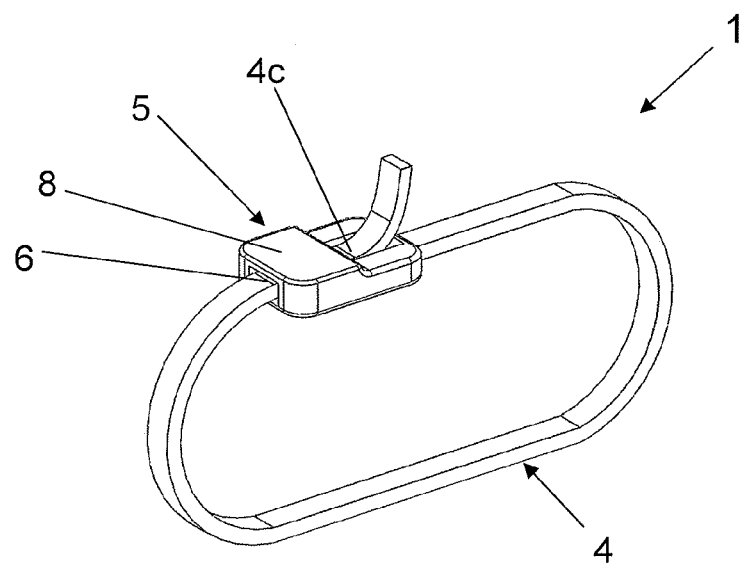
FIGS. 1 and 2 are perspective views of respective variants of a device not being part of the invention in which the strip forms a long enough loop so as to encircle the bone fragments to be fastened.
Figure 2:
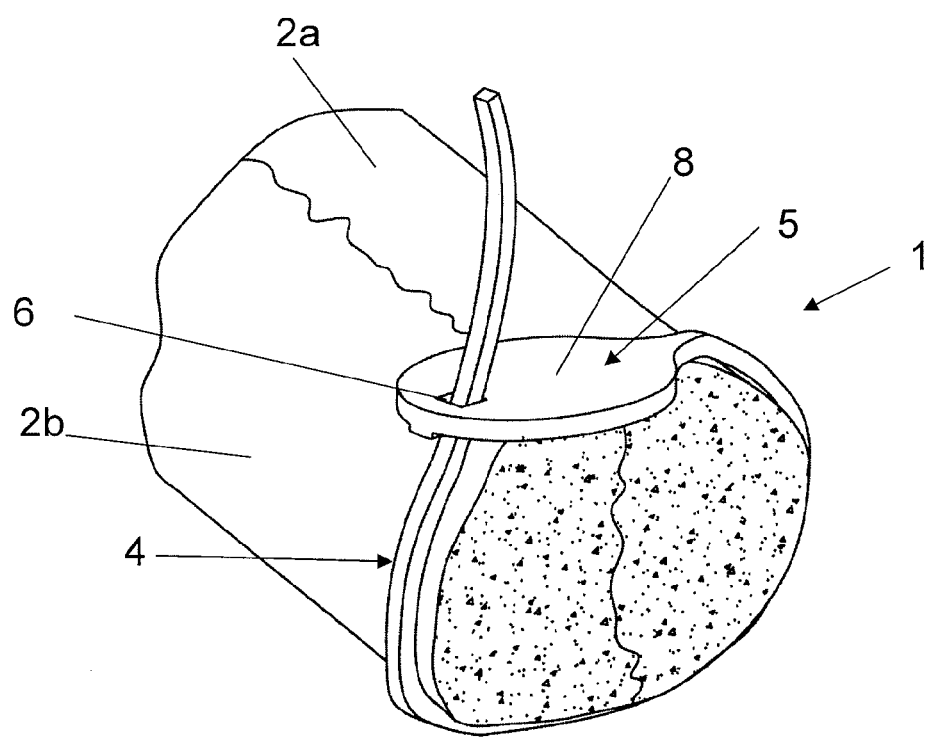

FIGS. 1 and 2 show first and second variants of the device 1 not being part of the invention for the joining of bone fragments, for example for the joining of two fragments 2*a* and 2*b* of a tibia (see FIG. 2).

The device 1 of FIG. 1 comprises a flexible strip 4, having a length allowing the formation of a fastening loop tightened around the bone fragments to be fastened, and irreversible fastening means 5 arranged at one of the ends of the strip 4. Said fastening means 5 are provided with an opening 6 which is provided with interlocking means 7 allowing the passage of the free end of the strip 4 and preventing its extraction in the direction opposite to its insertion.

In the variant of FIG. 1, the opening 6 for the passage of the fastening means 5 is oriented such that the portion of strip 4*c* retained by the interlocking means 7 is arranged such that it is essentially tangential to the formed loop, whereby the strip can completely hug the bone fragments, especially when the fractured bone has a circular section.

In the variant of FIG. 2, the fastening means 5 are arranged in an essentially planar closure plate 8 intended for being applied against the surface of the bone fragments 2*a* and 2*b*.

Figure 3:
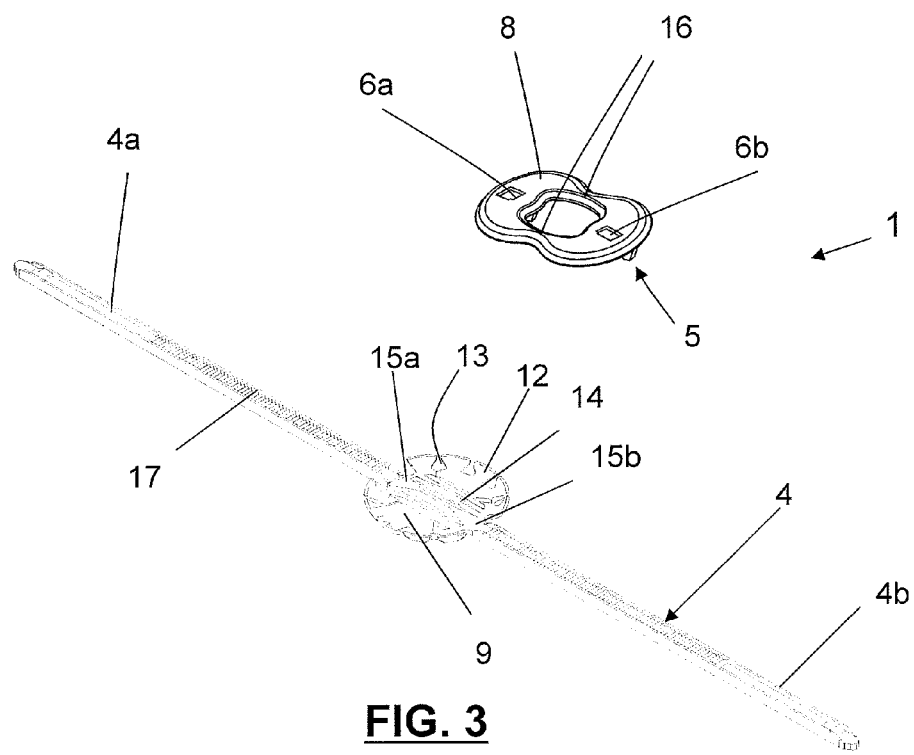
Figure 4:
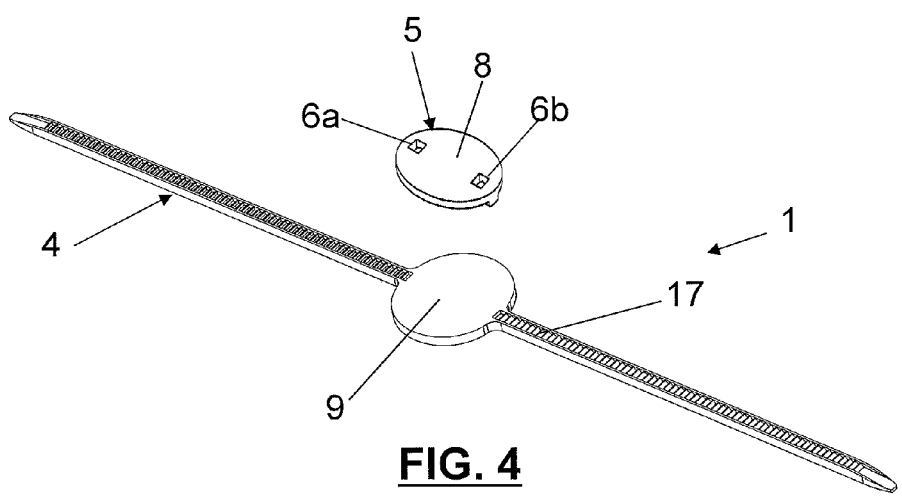

FIGS. 3 and 4 depict third and fourth variants of particular embodiments suitable for the fixation of a bone flap in an aperture made in the cranium or cranial bone mass. In both embodiments the device 1 comprises two plates connectable by means of the strip 4 flexible, one of which plates is a support plate 9, intended for being applied against the inner face of the mentioned bone fragments, and the other one is a closure plate 8, intended for being applied against the outer face of the mentioned bone fragments. The support plate 9 is a plate arranged between the two ends of the mentioned strip 4, respective opposing strip segments 4*a* and 4*b* being formed on both sides of the strip 4. The support plate 9 is integrally formed together with the body of the strip 4, forming a single body which adopts an essentially planar position when it is not operative.

With regard to the closure plate 8, it is detachable and provided with fastening means 5, which are provided with two openings 6*a*, 6*b* for the passage of respective opposite ends of the strip 4 for the formation of a closed loop as will be explained in detail below.

FIG. 3 shows that the support plate 9 is provided in its entire contour with multiple peripheral, flexible and elastic flanges 12, radially directed, in a somewhat inclined plane, from the plane of the support plate 9 towards the bone fragments on which said support plate 9 is intended to be supported. Advantageously, each flange 12 is separated from the adjacent flanges by respective cuts 13 made in the periphery of the support plate 9, such that the flanges 12 are wider at their outer end than at their joining to the support plate 9. The support plate 9 is likewise provided at its central portion with a plurality of ribs 14 arranged parallel to the plane in which the two strip segments 4a and 4b are inscribed.

It can also be seen in FIG. 3 that the strip segments 4a and 4b are joined diametrically opposite to the support plate 9 at respective areas of smaller section 15a, 15b than that of the rest of the support plate 9.

The areas of smaller section 15a and 15b along with the ribs 14 make it easier for the support plate 9 to adapt to the inner face of the cranial bone mass, allowing it to slightly bend, when the strip segments 4a and 4b exert pressure around the shaft marked by the direction of the ribs 14.

These features give the support plate 9 better gripping on the surface of the bone fragments and ensure that the strip 4, once the loop is formed and tightened, remains tensed due to the pulling effect that the flanges 12 transmit to the support plate 9 since the flanges want to recover their original position.

In the variant of FIG. 3, the closure plate 8 is provided with a partially weakened transverse area 16, suitable for giving the plate sufficient flexibility for the best possible coupling to the irregular configuration of the bone surface on which it must be supported. It thus achieves that the closure plate 8 can slightly bend along an imaginary line passing through the weakened areas of the closure plate 8, thus adapting to the outer face of the cranial bone mass, said shaft being advantageously perpendicular to the shaft which the support plate 9 bends, whereby achieving better support of the device 1 to the cranial bone mass.

Figure 5:
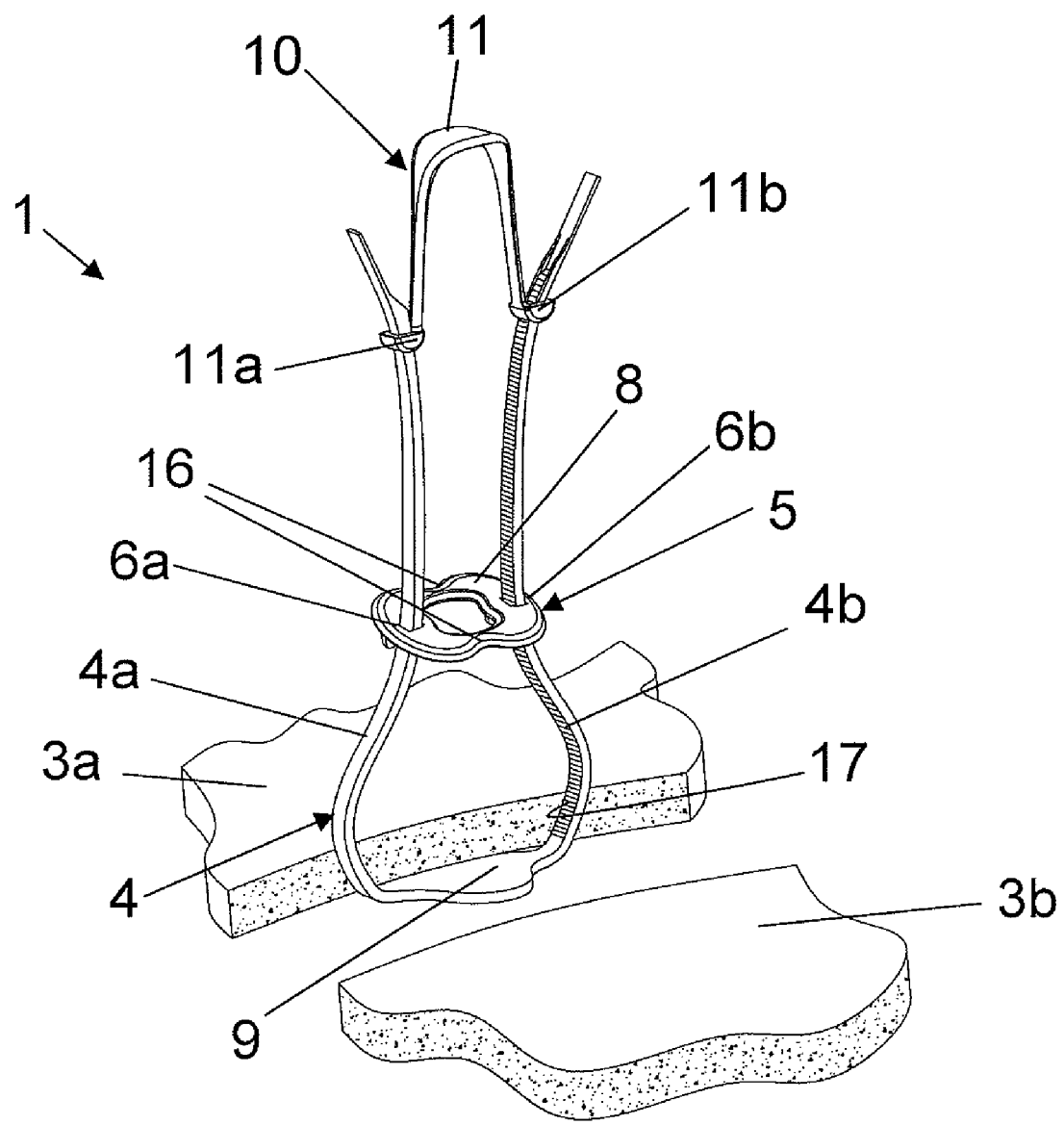

FIG. 5 depicts a device formed by the combination of a strip 4 according to the device according to FIG. 4 and a closure plate 8 according to the device of FIG. 3. In this FIG. 5 the free ends of the strip segments 4a and 4b have been inserted through the openings 6a and 6b, respectively, of the fastening means 5 provided for such purpose in the closure plate 8, a closed loop connecting the support plate 9 and the closure plate 8 having been formed.

Figure 6A:
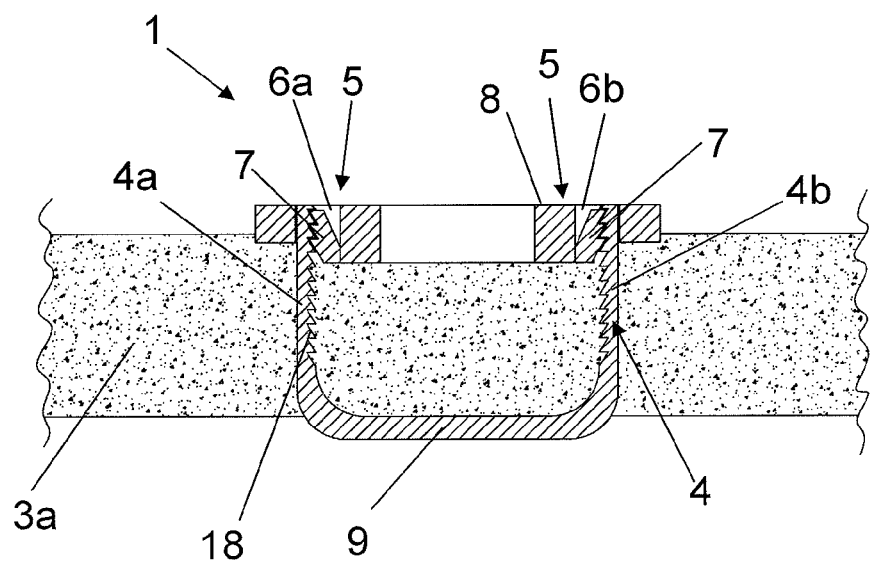
FIG. 6*a* is a section view of the device according to FIG. 4 in its operative position.

During the application of the device 1, the support plate 9 is first supported against the inner face of the outer edges of the cranial bone mass 3a and of the bone flap 3b, and the closure plate 8 subsequently slides along the strip segments 4a and 4b towards the outer face of the cranial bone mass 3a and the flap 3b until being applied against said outer face. Then the strip segments 4a and 4b are cut to the level of the closure plate 8, depicted in FIG. 6a, the device 1 thus being placed in an operative position.

For the purpose of making it easier to slide the closure plate 8 towards the bone mass, the invention envisages incorporating auxiliary gripping means to thus simultaneously grip both strip segments 4a and 4b and keep them tensed with one hand, such that with the other hand the closure plate 8 can be slid along the two strip segments 4a and 4b also simultaneously.

Figure 7:
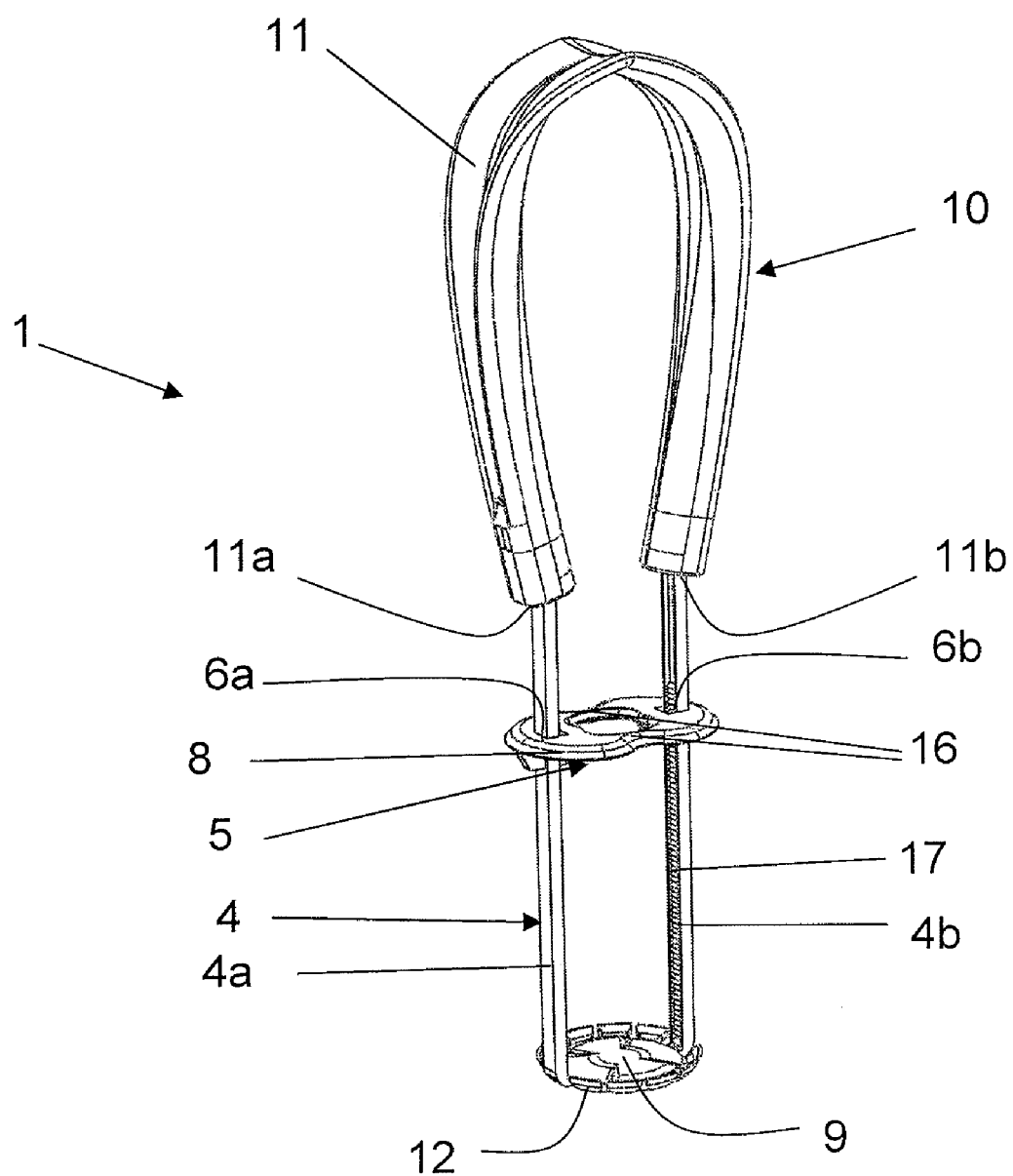

In the variants of FIGS. 5 and 7, the mentioned gripping means 10 are formed by a handle 11 the ends of which are provided with respective openings 11a and 11b provided with respective interlocking means allowing the passage of corresponding free ends of the segments 4a and 4b of the strip 4, preventing their extraction in the direction opposite to their insertion. These interlocking means can be formed similarly to the interlocking means, detailed below, provided in the openings 6a and 6b of the fastening means 5 of the closure plate 8.

Once the device 1 is positioned in the aperture of the cranium, the gripping means 10 prevent the support plate 9 from being moved and hitting against soft tissue (brain) and damaging it when the surgeon begins the movement of the closure plate 8 towards the support plate 9, without the need for additional instruments.

Figure 8:
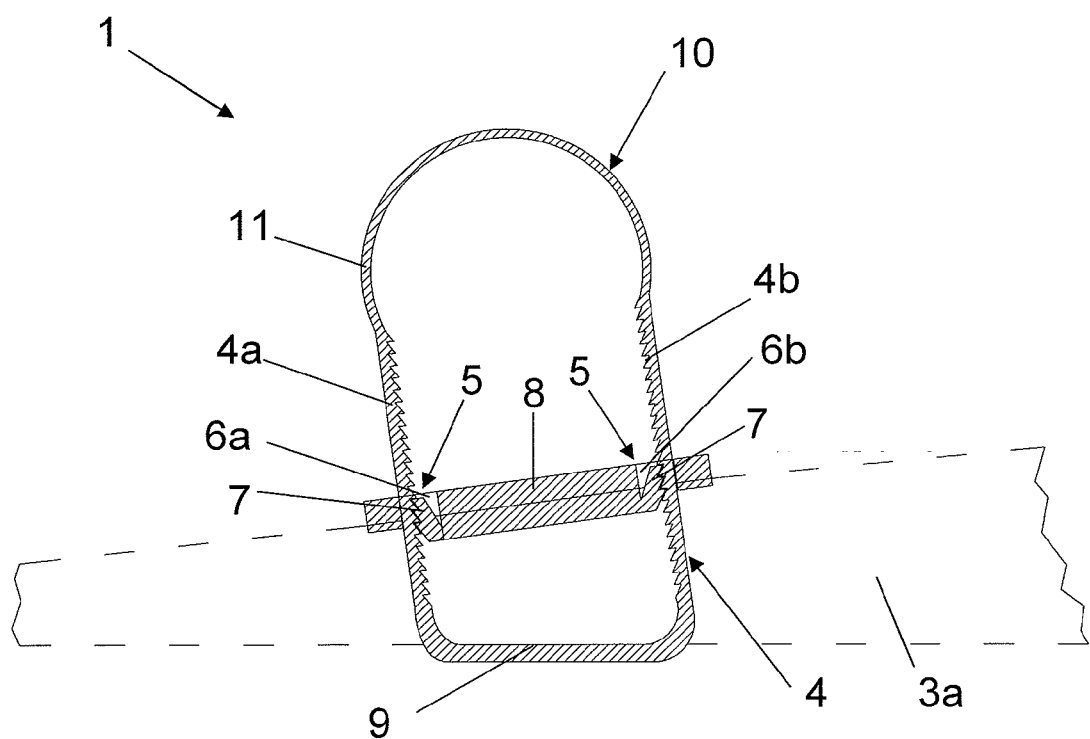
FIG. 8, is a view of a sixth variant of the invention, in an operative position, illustrating its adaptability to a cranium with irregular thickness.

Alternatively, said gripping means 10 can consist of, with an equivalent function, respective extensions perpendicular to the free ends of the strip segments 4a and 4b, like knobs. The gripping means 10 can also consist of the joining of the ends of the strip segments 4a and 4b, for example by fusing the materials forming them, as shown in FIG. 8.

Figure 6B:
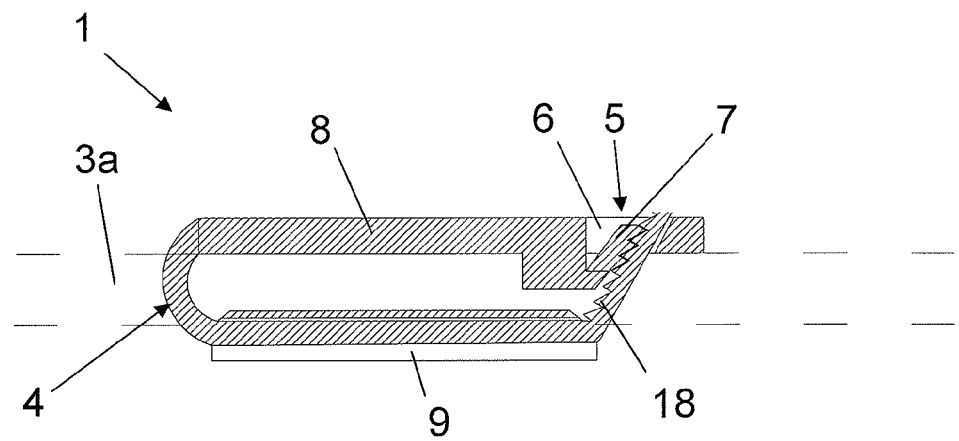
FIG. 6*b* is a view similar to that of FIG. 6*a* of a device according to a fifth variant of the invention.

FIG. 6b depicts another variant of the device according to the invention in which, unlike the devices of FIGS. 3 to 8, the closure plate 8 is integral with one of the ends of the strip 4, forming a single piece with it, and in which the fastening means 5 are provided with a single opening 6 for the passage of the opposite end of the strip 4. In this variant, for the purpose of being able to regulate the separation distance between the support plate 9 and the closure plate 8, adjusting it to the thickness of the cranial bone mass 3a, the support plate 9 is suitable for being longitudinally movable along the strip 4. For such purpose, the support plate 9 is preferably provided with a through opening longitudinally traversing the support plate 9, through which the strip 4 passes. According to another embodiment, the support plate 9 can be provided with a longitudinal groove in its outer face, having a width similar to the width of the strip 4, inside of which the mentioned strip 4 would be tightly housed when the loop is formed and the support plate 9 is applied, under pressure, against the inner face of the bone mass.

This variant of the invention can also apply in the case of wanting to join cracked or broken bone fragments, such as bones with considerably circular cross section (tibias, fibulas, ulnas, ribs, etc.). It can also apply in operations in which the sternum must be cut along the longitudinal axis, for example, when it is necessary to access the organs in the upper part of the chest, such as the heart or lungs.

The fastening means 5 of the device 1 are commonly arranged in the closure plate 8 in all the variants of the device 1 depicted in FIGS. 2 to 8. Even though in some variants the fastening means are provided with two openings for the passage of two free ends of the strip 4 and in other variants with a single opening, these openings have a contour that is complementary or similar to the cross section of the strip 4 and are provided with interlocking means 7 visible in the examples of FIGS. 6a, 6b and 8.

The mentioned interlocking means 7 consist of an elastic tab, formed integrally with the body of the closure plate 8, having a catch effect, cooperating with a ratchet tooth system provided at least at the apical ends or end of the strip 4. The ratchet tooth system comprises a rough surface 17 on at least one of the faces of the strip 4, there being formed a series of consecutive projections 18 suitable for collaborating with the interlocking means 7 of the opening or openings, as the case may be, through which the strip 4 is passed. The elastic tabs prevent and block the backward movement of the strip 4, ensuring the closure of the formed loop.

Preferably, the rough surface 17 is provided only on the inner face of the strip 4, because damage to adjacent structures is thus prevented.

The device 1 according to the invention is widely advantageous in its transport and use because first in its inoperative position of storage or distribution, it takes up little space and can be completely planar without later compromising its functionality. This inoperative position makes it easier to transport and distribute the devices 1, which can be stored or distributed in small size and small volume packages, such as envelopes or relatively thin cases.

In addition, the device 1 allows being applied to individuals with variations regarding the thickness of the bone since long enough strips 4 are envisaged for being adapted to different bone thicknesses. Furthermore, the same device 1 perfectly adapts, without the formation of projections, being uniformly tensed on its entire surface, to the different thicknesses that may existing in one and the same bone fragment of an individual.

This is particularly relevant because the reality of individuals indeed shows that one and the same person may present thickness variations in one and the same bone, not just because of anatomy but also because of particularities of each individual. It is thus known that the cranium presents areas of different thicknesses, but furthermore, these areas are also subject to variability between individuals. All this inter- and intra-individual variability is solved with the fixation device 1 object of the invention, as shown in FIG. 8.

With a device 1 according to any one of the variants depicted in FIGS. 1 to 8, operations can be performed in a wide range of people of different ages and sexes, or even in different animal species.

Furthermore, the devices 1 are easy to manufacture by common material molding or injection techniques.

Regarding the type of materials used for the manufacture of the fixation device 1 according to the invention, it is possible to use any material of those known as biocompatible polymeric material, biocompatible metal allows, ceramics or composites of the foregoing. Generally, biocompatible, implantable and/or osteo-integratable materials are chosen, i.e., materials producing minimum reaction when introduced in the animal or human body and which can furthermore make the neoformation or regeneration of bone tissue easier, the device be osteo-integrated and/or finally reabsorbed by the body after sufficient time has passed for the groove, opening or cut to have been filled in with new tissue. These materials can furthermore be radiotransparent.

The invention claimed is:

1. A fixation device for fixation of bone fragments, comprising:
   two plates connected by a flexible strip, the two plates and flexible strip collectively forming one and only one loop to fasten the bone fragments, the strip comprising a first free end and an opposite second free end;
   one of the plates is a closure plate loaded onto the flexible strip and adapted to be applied against one face of the bone fragments;
   the other of the plates is a support plate adapted to be applied against another face of the bone fragments;
   the closure plate comprises a first opening and a second opening, the first opening configured to allow insertion of the first free end and prevent extraction of the strip in a direction opposite to the insertion of the first free end, and the second opening configured to allow insertion of the second free end and prevent extraction of the strip in a direction opposite to insertion of the second free end;
   the support plate arranged intermediate to the first free end and the second free end of the strip with opposing strip segments extending from the support plate, the support plate and the flexible strip being monolithic.

2. The fixation device according claim 1, wherein the opposing strip segments extend from opposite boundaries of the support plate.

3. The fixation device according to the claim 1, further comprising an auxiliary gripping device formed by a handle that is attached to the flexible strip, the handle comprising two openings provided with an interlocking mechanism that allows insertion of the first and second free ends, respectively, and that prevents extraction of the strip in the direction opposite to the insertion.

4. The fixation device according to claim 1, wherein the support plate is provided with multiple flexible flanges extending radially from an outer periphery of the support plate.

5. The fixation device according to claim 4, wherein the flanges are inclined relative to the plane of the support plate and extend towards the bone fragments on which the support plate rests when applied to the bone fragments, each flange is an integral one-piece construction with the support plate.

6. The fixation device according to claim 5, wherein the support plate comprises a plurality of ribs extending parallel to the longitudinal direction of the strip.

7. The fixation device according to claim 1, wherein the closure plate is provided with a partially weakened transverse area giving the closure plate sufficient flexibility to conform to the face of the bone fragments against which the closure plate is applied.

8. The fixation device according to claim 1, wherein each of the opposing strip segments comprises teeth and each of the first opening and second opening of the closure plate comprise a flexible tab that cooperates with the teeth to prevent the extraction of the strip.

9. The fixation device according to claim 1, wherein the closure plate and the support plate are configured for fixation of a bone flap in the cranium.

10. A fixation device made of biocompatible material for the fixation of bone fragments, applicable to the mutual fastening of bone fragments temporarily separated during a surgical operation or trauma and particularly intended for the fixation of a bone flap in the replacement thereof in a corresponding aperture made in the cranium or cranial bone mass, the fixation device comprising two plates connected by a flexible strip having a length allowing the formation of one and only one fastening loop tightly fastening the bone fragments to be joined together, one of said plates is a closure plate loaded onto the flexible strip and adapted to be applied against one face of the bone fragments and provided with irreversible fastening means for the flexible strip; and the other plate is a support plate for being applied against another face of the bone fragments, wherein the fastening means are provided with two openings for the passage of respective opposite free ends of the strip provided with interlocking means comprising elastic tabs allowing the passage of said respective ends of the strip for insertion of the strip and preventing extraction of the strip in a direction opposite to the insertion of the strip, and wherein the support plate is arranged between the two ends of the strip, the support plate and the strip being monolithic, in a way that respective opposing strip segments extend from a boundary of said support plate forming an assembly which is susceptible of adopting an essentially planar position in an inoperative position prior to the closure plate being loaded onto the flexible strip, the device adapted to be placed in an upright operative position once the one and only one fastening loop is formed, and subsequently to an operative position by sliding the closure plate along the strip towards the support plate.

11. The device according to the claim 10, further comprising auxiliary gripping means formed by a handle the ends of which are provided with respective openings provided with interlocking means allowing the passage of a corresponding free end of the strip and preventing extraction of the corresponding free end of the strip in the direction opposite to the insertion.

12. The device according to claim 10, wherein an entire contour of the support plate is provided with multiple peripheral, flexible and elastic flanges, radially directed, in a somewhat inclined plane, from the plane of the plate towards the bone fragments on which the plate is supported, each flange being separated from the adjacent flanges by respective cuts made in the periphery of the plate, which determining flanges that are wider at their outer end than at their joint to the plate; and in that the support plate is provided in a central portion with a plurality of ribs arranged parallel to the plane of the flexible strip.

13. The device according to claim 12, wherein the support plate is arranged integral with the central portion of the flexible strip and is joined to said strip by respective, diametrically opposite, areas of smaller section than that of the rest of the support plate.

14. The device according to claim 10, wherein the closure plate is provided with a partially weakened transverse area, suitable for giving the closure plate sufficient flexibility for the best possible coupling to the irregular configuration of the bone surface on which said closure plate must be supported.

15. The device according to claim 10, wherein the strip is provided with a rough surface on at least one face of the strip, a series of projections being formed which are suitable for collaborating with the interlocking means of the opening or openings, of the irreversible fastening means.

* * * * *